US00PP15994P2

(12) United States Plant Patent
Roberson

(10) Patent No.: US PP15,994 P2
(45) Date of Patent: Sep. 27, 2005

(54) ***CLEOME* PLANT NAMED 'ROBSPIFRO'**

(50) Latin Name: *Cleome hasslerana*
Varietal Denomination: Robspifro

(76) Inventor: Robert J. Roberson, 31706 E. Pink Hill Rd., Grain Valley, MO (US) 64029

( * ) Notice: Subject to any disclaimer, the term of this patent is extended or adjusted under 35 U.S.C. 154(b) by 71 days.

(21) Appl. No.: 10/882,876

(22) Filed: Jul. 1, 2004

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—C. A. Whealy

(57) ABSTRACT

A new and distinct cultivar of *Cleome* plant named 'Robspifro', characterized by its upright and compact plant habit; large inflorescences with numerous flowers; white-colored flowers; and tolerance to high temperatures.

1 Drawing Sheet

Botanical classification/cultivar designation: *Cleome hasslerana* cultivar Robspifro.

BACKGROUND OF THE INVENTION

The present Invention relates to a new and distinct cultivar of *Cleome* plant, botanically known as *Cleome hasslerana*, and hereinafter referred to by the name 'Robspifro'.

The new *Cleome* is a product of a planned breeding program conducted by the Inventor in Grain Valley, Mo. The objective of the breeding program was to develop new consistently compact *Cleome* cultivars.

The new cultivar originated from a cross-pollination made by the Inventor in 2001 of two unknown selections of *Cleome hasslerana*, not patented. The cultivar Robspifro was discovered and selected by the Inventor in July, 2002 as a single flowering plant within the progeny of the stated cross-pollination in a controlled environment in Grain Valley, Mo.

Asexual reproduction of the new *Cleome* by tip cuttings at Grain Valley, Mo. since 2002, has shown that the unique features of this new *Cleome* are stable and reproduced true to type in successive generations of asexual reproduction.

SUMMARY OF THE INVENTION

The following traits have been repeatedly observed and are determined to be the unique characteristics of 'Robspifro'. These characteristics in combination distinguish 'Robspifro' as a new and distinct cultivar:

1. Upright and compact plant habit.
2. Large inflorescences with numerous flowers.
3. White-colored flowers.
4. High temperature tolerant.

Plants of the new *Cleome* can be compared to plants of the parental selections. Compared to plants of the parental selections, plants of the new *Cleome* are more compact.

Plants of the new *Cleome* can be compared to plants of the seed-propagated *Cleome* Queen series, not patented. Compared to plants of the Queen Series, plants of the new *Cleome* are more compact and have larger inflorescences.

Plants of the new *Cleome* can also be compared to plants of the seed-propagated *Cleome* Sparkler series, not patented. Compared to plants of the Sparkler Series, plants of the new

*Cleome* are more uniform in plant growth habit and flower coloration.

BRIEF DESCRIPTION OF THE PHOTOGRAPHS

The accompanying colored photographs illustrate the overall appearance of the new *Cleome*, showing the colors as true as it is reasonably possible to obtain in colored reproductions of this type. Colors in the photographs may differ slightly from the color values cited in the detailed botanical description which accurately describe the colors of the new *Cleome*.

The photograph at the bottom of the sheet comprises a side perspective view of typical plants of 'Robspifro'.

The photograph at the top of the sheet is a close-up view of typical plants of 'Robspifro'.

DETAILED BOTANICAL DESCRIPTION

The new *Cleome* has not been observed under all possible environmental conditions. The phenotype may vary somewhat with variations in environment such as temperature and light intensity, without, however, any variance in genotype.

The aforementioned photographs, following observations and measurements describe plants grown in Grain Valley, Mo. in an outdoor nursery during the summer and under commercial production practices. During the day, temperatures averaged 32° C. and night temperatures averaged 24° C. Plants were about five months old when the photographs and description were taken. In the following description, color references are made to The Royal Horticultural Society Colour Chart, 1995 Edition, except where general terms of ordinary dictionary significance are used.

Botanical classification: *Cleome hasslerana* cultivar Robspifro.

Parentage:

*Female, or seed, parent.*—Unknown selection of *Cleome hasslerana*, not patented.

*Male, or pollen, parent.*—Unknown selection of *Cleome hasslerana*, not patented.

Propagation:

*Type.*—Tip cuttings.

*Time to initiate roots.*—About one week at 27° C.

*Time to produce a rooted young plant.*—About 12 days at 24° C.

*Root description.*—Freely branching; fibrous; white to brown in color.

Plant description:

*Plant form/growth habit.*—Compact plant habit; upright plant form. Strong and erect stems. Moderately vigorous growth habit. Plants not freely branching.

*Plant height.*—About 70 cm.

*Plant width.*—About 20 cm.

*Stem description.*—Length: About 70 cm. Diameter: About 6 mm. Internode length: About 1.3 cm. Strength: Strong. Angle: Upright. Texture: Pubescent; viscid. Color: Close to 144A.

*Foliage description.*—Leaves palmately compound with about five leaflets per leaf. Leaflet length: About 3.75 cm. Leaflet width: About 1 cm. Leaflet shape: Lanceolate to ovate. Leaflet apex: Acute. Leaflet base: Attenuate. Leaflet margin: Entire. Leaflet texture, upper and lower surfaces: Slightly pubescent; viscid. Fragrance: Pungent. Leaflet venation pattern: Pinnate. Leaflet color: Developing leaflets, upper surface: 138A. Developing leaflets, lower surface: 138B. Fully expanded leaflets, upper surface: 137C. Fully expanded leaflets, lower surface: 137D. Venation, upper and lower surfaces: Similar to lamina. Leaf petiole: Length: About 2.4 cm. Diameter: About 1 mm. Texture, upper and lower surfaces: Pubescent. Color, upper and lower surfaces: Close to 144A.

Flower description:

*Flower type and habit.*—Numerous single flowers arranged on large terminal racemes. Flowers persistent. Flowers face upright and outwardly. Flowers not fragrant.

*Natural flowering season.*—Plants flower in the landscape from May until frost in Grain Valley, Mo.; during this period flowering recurrent.

*Postproduction longevity.*—Flowers typically last about one to two weeks on the plant.

*Flower buds.*—Height: About 2 cm. Diameter: About 8 mm. Shape: Ovoid. Color: 155C.

*Inflorescence height.*—About 10 cm.

*Inflorescence diameter.*—About 20 cm.

*Flowers.*—Diameter: About 4 cm. Depth: About 2.5 cm.

*Petals.*—Quantity per flower: About four in a single whorl. Length: About 2 cm. Width: About 1.25 cm. Shape: Obovate. Apex: Obtuse to acute. Base: Attenuate. Margin: Entire. Texture, upper and lower surfaces: Smooth, glabrous. Color: Developing, upper and lower surfaces: 155C. Fully expanded, upper and lower surfaces: 155C.

*Sepals.*—Quantity per flower: Five. Length: About 5 mm. Width: About 1 mm. Shape: Lanceolate. Apex: Sharply acute. Base: Fused. Margin: Entire. Texture, upper and lower surfaces: Smooth. Color, upper surface: Close to 138A. Color, lower surface: Close to 138B.

*Pedicels.*—Length: About 1.3 cm. Diameter: Less than 1 mm. Orientation: Initially erect, then horizontal. Strength: Strong. Color: Close to 144A.

*Reproductive organs.*—Stamens: Quantity per flower: About eight. Anther shape: Oblong. Anther length: Less than 1 mm. Filament length: About 4.4 cm. Filament color: 155C. Pollen amount: Not observed. Pistils: Quantity per flower: One. Pistil length: About 4.7 cm. Stigma shape: Rounded. Style length: About 4.5 cm. Style color: 157A. Ovary color: Close to 144A.

*Fruit.*—Length: About 1 cm. Diameter: About 1.5 mm. Color: Close to 144A.

Pathogen/pest resistance: Plants of the new *Cleome* have not been observed to be resistant to pests and pathogens common to *Cleomes*.

Garden performance: Plants of the new *Cleome* have been observed have good garden performance and to tolerate rain, wind and temperatures ranging from 10 to 41° C.

It is claimed:

1. A new and distinct cultivar of *Cleome* plant named 'Robspifro', as illustrated and described.

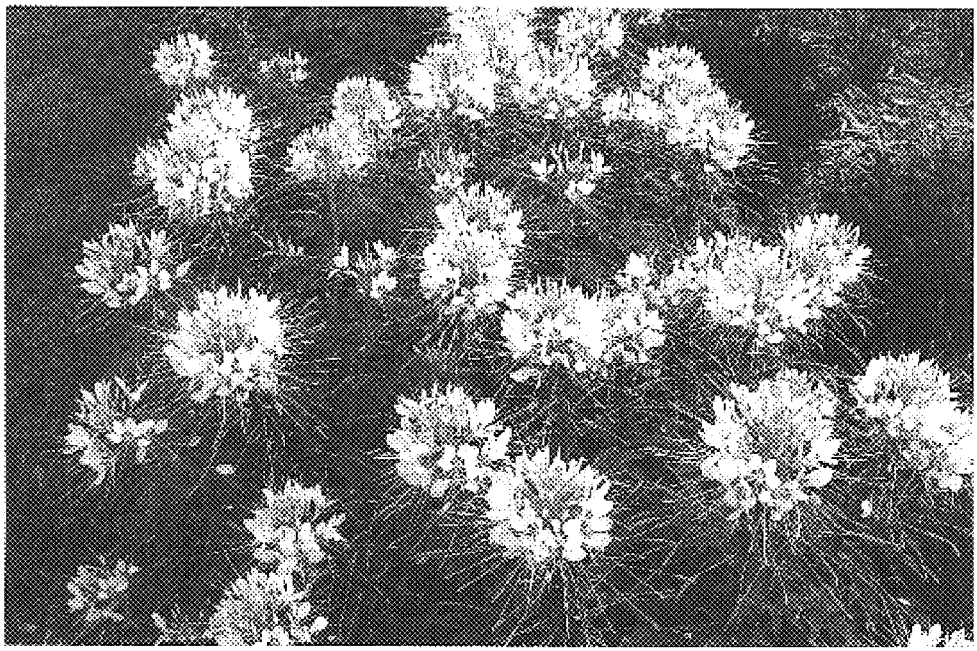
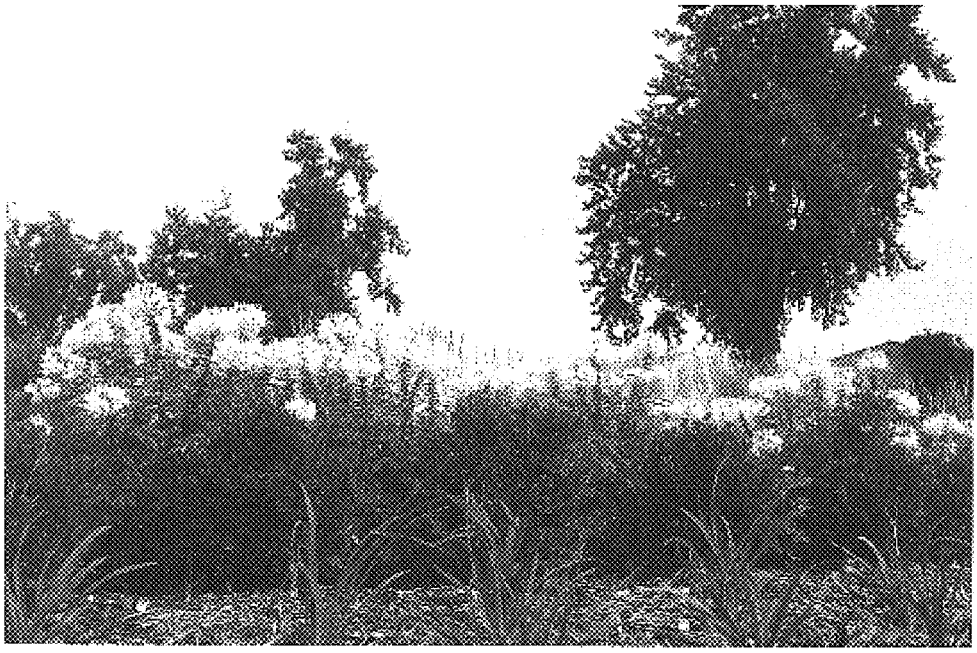

* * * * *